(12) United States Patent
Takahashi et al.

(10) Patent No.: US 9,101,339 B2
(45) Date of Patent: Aug. 11, 2015

(54) ENDOSCOPE APPARATUS

(75) Inventors: Kazuhiko Takahashi, Hachioji (JP); Toshio Nakamura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1438 days.

(21) Appl. No.: 12/549,779

(22) Filed: Aug. 28, 2009

(65) Prior Publication Data

US 2009/0326319 A1     Dec. 31, 2009

Related U.S. Application Data

(63) Continuation of application No. PCT/JP2007/070948, filed on Oct. 26, 2007.

(30) Foreign Application Priority Data

Mar. 2, 2007    (JP) .................. 2007-053108

(51) Int. Cl.
*A61B 1/00* (2006.01)
*A61B 1/04* (2006.01)
*A61B 17/00* (2006.01)
*A61B 19/00* (2006.01)
*A61B 1/018* (2006.01)
*A61B 17/29* (2006.01)
*A61B 18/14* (2006.01)

(52) U.S. Cl.
CPC ........... *A61B 17/00234* (2013.01); *A61B 19/22* (2013.01); *A61B 1/018* (2013.01); *A61B 17/29* (2013.01); *A61B 18/1492* (2013.01); *A61B 2017/003* (2013.01); *A61B 2017/00353* (2013.01); *A61B 2019/2249* (2013.01); *A61B 2019/2269* (2013.01)

(58) Field of Classification Search
USPC .................. 600/104, 106, 107, 114–116, 118, 600/139–152, 117; 606/1, 205–209; 604/95.01–95.05
See application file for complete search history.

(56) References Cited

U.S. PATENT DOCUMENTS

2005/0250989 A1 * 11/2005 Suzuki ..................... 600/106
2006/0276784 A1    12/2006 Miyajima et al.

FOREIGN PATENT DOCUMENTS

EP    1728462 A2 * 12/2006 .............. A61B 1/00
JP    03149022 A * 6/1991 ............... A61B 1/00
JP    4-164434     6/1992

(Continued)

OTHER PUBLICATIONS

Chinese Office Action dated Jan. 27, 2011 together with an English language translation.

*Primary Examiner* — Ryan Henderson
(74) *Attorney, Agent, or Firm* — Scully, Scott, Murphy & Presser, P.C.

(57) ABSTRACT

An endoscope apparatus includes an accessory including an actuation portion configured to be actuated, an operating unit for operating the actuation portion, an endoscope including an accessory insertion pass wherein the accessory is adapted to be inserted through the accessory insertion pass from a proximal end portion of the accessory insertion pass to a distal end portion of the accessory insertion pass, and projected from and retracted into the distal end portion of the accessory insertion pass, a detecting unit configured to detect a condition of a part of the accessory, which is projected from the distal end portion of the accessory insertion pass, and a control unit configured to control an actuation of the actuation portion by an operation to the operating detecting unit.

9 Claims, 8 Drawing Sheets

(56) References Cited

FOREIGN PATENT DOCUMENTS

| JP | 9-262241 | 10/1997 | | |
| JP | 2004141486 A | * 5/2004 | ............... | A61B 1/00 |
| JP | 2004-337187 | 12/2004 | | |
| JP | 2006-26013 | 2/2006 | | |
| JP | 2006-280592 | 10/2006 | | |
| JP | 2006-326157 | 12/2006 | | |

* cited by examiner

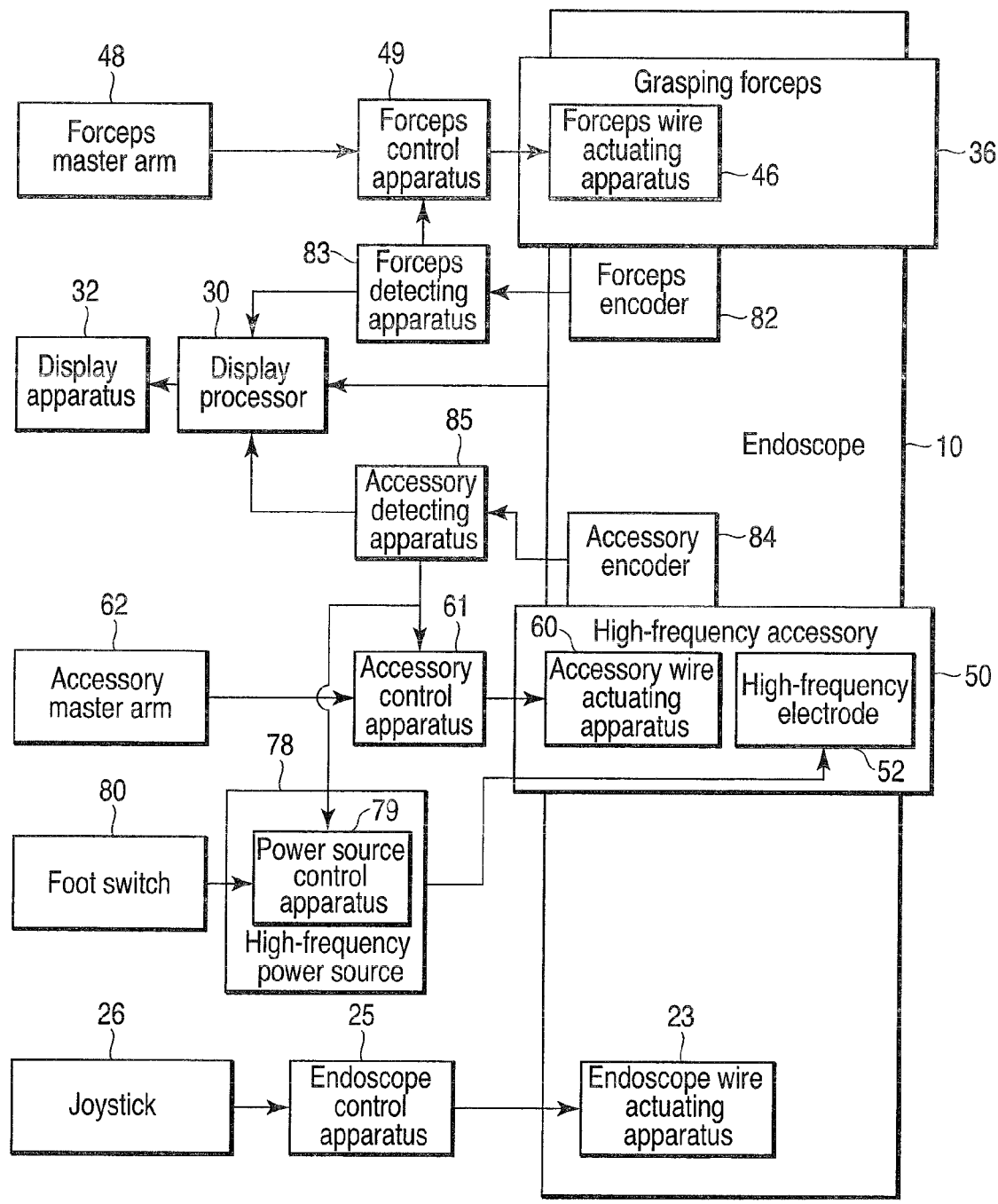
F I G. 2

ENDOSCOPE APPARATUS

CROSS-REFERENCE TO RELATED APPLICATIONS

This is a Continuation Application of PCT Application No. PCT/JP2007/070948, filed Oct. 26, 2007, which was published under PCT Article 21(2) in Japanese.

This application is based upon and claims the benefit of priority from prior Japanese Patent Application No. 2007-053108, filed Mar. 2, 2007, the entire contents of which are incorporated herein by reference.

BACKGROUND OF THE INVENTION

1. Field of the Invention

The present invention relates to an endoscope apparatus including an endoscope and an accessory adapted to be inserted through an accessory insertion pass of the endoscope.

2. Description of the Related Art

An endoscope apparatus is used. In the endoscope apparatus, an endoscope is inserted into a cavity in the body, an accessory is projected from the distal end portion of the endoscope through an accessory insertion pass of the endoscope, and a treatment is performed in the cavity in the body under an observation of the endoscope.

In an endoscope apparatus disclosed in Jpn. Pat. Appln. KOKAI Publication No. 9-262241, a grasping forceps is used as an accessory. In the grasping forceps, a grasping portion is provided on the distal end portion thereof and configured to be operated to be opened and closed. The grasping forceps is adapted to be put into an accessory inlet portion on the proximal end portion of the endoscope, inserted through an accessory insertion pass, and put out from an accessory outlet portion of the distal end portion of the endoscope. A detecting means is provided on the proximal end portion of the grasping forceps, and an amount of a projection of the grasping portion from the accessory outlet portion can be perceived on the basis of a relative positional relationship between the detecting means and the accessory outlet potion. Furthermore, the detecting means may be given a function for limiting a maximum amount of a projection of the grasping portion from the accessory outlet portion.

BRIEF SUMMARY OF THE INVENTION

In an aspect of the present invention, an endoscope apparatus includes: an accessory including an actuation portion configured to be actuated; an operating unit for operating the actuation portion; an endoscope including an accessory insertion pass wherein the accessory is adapted to be inserted through the accessory insertion pass from a proximal end portion of the accessory insertion pass to a distal end portion of the accessory insertion pass, and projected from and retracted into the distal end portion of the accessory insertion pass; a detecting unit configured to detect a condition of a part of the accessory, which is projected from the distal end portion of the accessory insertion pass; and a control unit configured to control an actuation of the actuation portion by an operation to the operating unit, on the basis of a result of detection by the detecting unit.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a block diagram showing the endoscope system according to the first embodiment of the present invention;

DETAILED DESCRIPTION OF THE INVENTION

Figure 1:
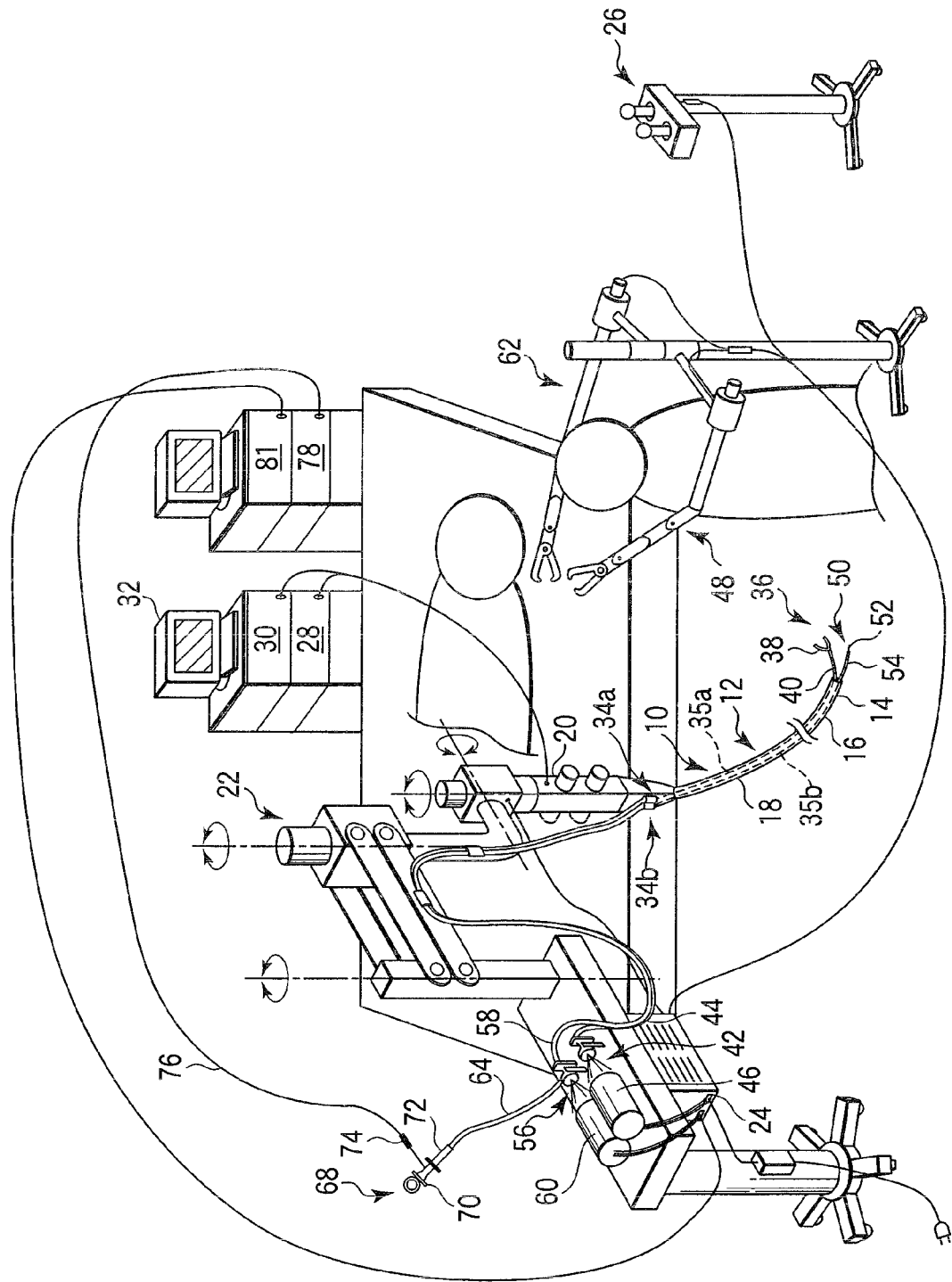
FIG. 1 is a schematic view showing the endoscope system according to a first embodiment of the present invention.

Hereinafter, a first embodiment of the present invention will be explained referring to the drawings.

Referring to FIGS. 1 and 2, an active endoscope 10 (simply referred to as an endoscope 10 hereinafter) of an endoscope treatment system includes an endoscope insertion portion 12 configured to be inserted into a cavity in the body. In the endoscope insertion portion 12, a distal end rigid portion 14 being rigid, an endoscope bending portion 16 configured to be actuated to be bent and an endoscope insertion tube portion 18 being long and flexible are provided in order from the distal end side, and an endoscope operation portion 20 is coupled to the proximal end portion of the endoscope insertion portion 12. The endoscope operation portion 20 is placed on, and attachable to and detachable from the distal end portion of a movable type of endoscope stand 22 and the movable type of endoscope stand 22 is configured to move and fix the endoscope operation portion 20 to and in any position.

Endoscope angle wires for operating the endoscope bending portion 16 to be bent are inserted through the endoscope bending portion 16 and the endoscope insertion tube portion 18. The endoscope angle wires are put into the endoscope operation portion 20 from the endoscope insertion tube portion 18, and coupled to an endoscope wire actuating apparatus 23 in the endoscope operation portion 20. The endoscope wire actuating apparatus 23 is connected to an endoscope control apparatus 25 of a control unit 24 provided on the movable type of endoscope stand 22, and a joystick 26 is connected to the endoscope control apparatus 25. When operating the joystick 26, the endoscope wire actuating apparatus 23 moves forward and backward the endoscope angle wires and the endoscope bending portion 16 is actuated to be bent.

Moreover, the endoscope 10 is connected to a light source apparatus 28 and a display processor 30 carried on the endoscope trolley. Illumination light is supplied from the light source apparatus 28 to the endoscope 10 and emitted from the distal end portion of the endoscope 10, an observation image is obtained by an image pick-up unit in the distal end portion of the endoscope 10, an image signal of the observation image is output to a display processor 30, and the observation image is displayed on a display apparatus 32.

Furthermore, a forceps insertion inlet 34a and an accessory insertion inlet 34b are provided on the endoscope operation portion 20, and a forceps channel 35a and a accessory channel 35b as an accessory insertion pass are extended from the forceps insertion inlet 34a and the accessory insertion inlet 34b to the distal end portion of the endoscope 10, respectively.

An active grasping forceps 36 (simply referred to as a grasping forceps 36 hereinafter) as an accessory is adapted to be inserted through the forceps channel 35a of the endoscope 10 so as to be movable forward and backward. In the grasping forceps 36, a grasping portion 38 configured to be actuated to be opened and closed, a forceps bending portion 40 configured to be actuated to be bent and rotated and a forceps insertion tube portion 44 being long and flexible are provided in order from the distal end side.

Figure 3A:
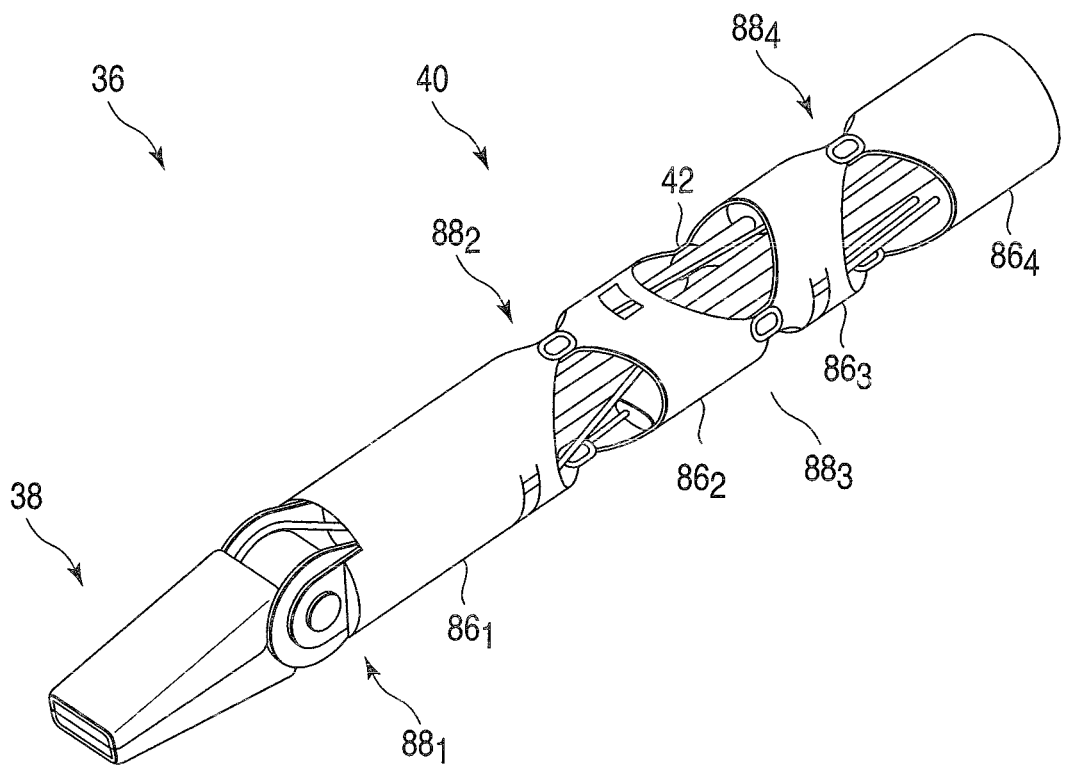
FIG. 3A is a perspective view showing a distal end portion of a grasping forceps according to the first embodiment of the present invention.
Figure 3B:
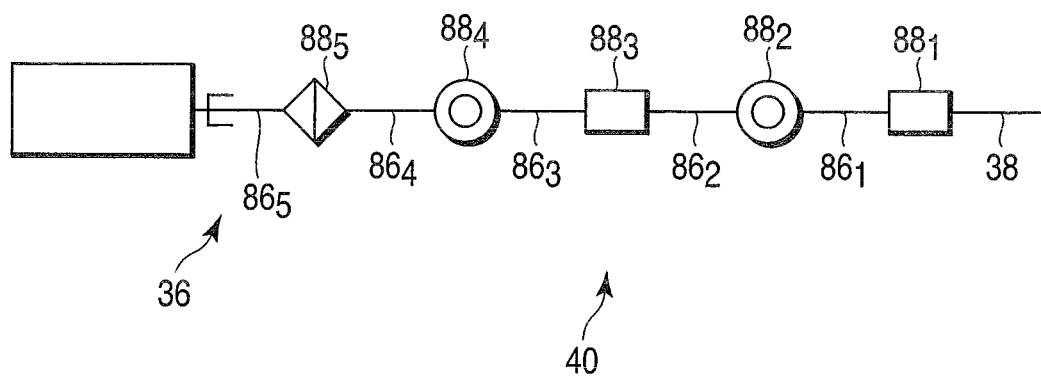
FIG. 3B is a schematic view showing the distal end portion of the grasping forceps according to the first embodiment of the present invention.

Referring to FIGS. 3A and 3B, a structure of the distal end portion of the grasping forceps 36 will be explained in detail.

In the distal end portion of the grasping forceps 36, the grasping portion 38 and a first to a fifth substantially circular cylindrical forceps bending part $86_1$, $86_2$, $86_3$, $86_4$, $86_5$ are coupled in order so as to be substantially coaxial through a first to a fifth forceps joint portion $88_1$, $88_2$, $88_3$, $88_4$, $88_5$. In the grasping portion 38, a pair of jaws is configured to be opened and closed about a pivot axis which is a rotational axis of the first forceps joint portion $88_1$. Furthermore, the grasping portion 38 and the first to the fourth forceps bending part $86_1$ ... $86_4$ are rotatable relative to each other about a rotational axis of the first to the fourth forceps joint portion $88_1$ ... $88_4$, respectively, and the rotational axes of the forceps joint portions $88_1$ ... $88_5$ adjacent to each other are substantially orthogonal to each other. The fourth forceps bending part $86_4$ is coupled to the fifth forceps bending part $86_5$ through the fifth forceps joint portion $88_5$. A rotational axis of the fifth forceps joint portion $88_5$ substantially corresponds to the central axis of the fourth and the fifth forceps bending part $86_4$, $86_5$, and the fourth forceps bending part $86_4$ is rotatable about the central axis of itself relative to the fifth forceps bending part $86_5$. The distal end portions of forceps angle wires 42 for actuating the grasping portion 38 to be opened and closed and the first to the fifth forceps joint portion $88_1$ ... $88_5$ to be rotated are connected to the first forceps joint portion $88_1$, the first to the third forceps bending part $86_1$ ... $86_3$, and the fifth forceps joint portion $88_5$, respectively. In this way, the grasping portion 38, the first to the fifth forceps joint portion $88_1$ ... $88_5$ forms actuation portions, respectively. The forceps angle wires 42 are inserted through the forceps bending portion 40 and the forceps insertion tube portion 44 and extended to the proximal end side.

Referring to FIGS. 1 and 2 again, the forceps insertion tube portion 44 is put out from the accessory channel 35b and extended to a forceps wire actuating apparatus 46 provided on the movable type of endoscope stand 22, and the forceps angle wires 42 put out from the proximal end portion of the forceps insertion tube portion 44 are coupled to the forceps wire actuating apparatus 46. The forceps wire actuating apparatus 46 is connected to a forceps control apparatus 49 as a grasping portion control unit and a joint portion control unit of the control unit 24, and a forceps master arm 48 as a grasping portion operating unit and a joint portion operating unit is connected to the forceps control apparatus 49. The forceps master arm 48 has a degree of freedom similar to that of the grasping portion 38 and the forceps bending portion 40 of the grasping forceps 36. When operating the forceps master arm 48, the forceps wire actuating apparatus 46 operates the forceps angle wires 42 to be moved forward and backward, and the grasping portion 38 is actuated to be opened and closed and the forceps bending portion 40 is actuated to be bent and rotated according to an operation to the forceps master arm 48, in a normal mode.

Furthermore, a forceps roller is provided on the proximal end portion of the forceps channel 35a and configured to be rotated according to a forward and backward movement of the grasping forceps 36. A forceps encoder 82 is provided in the forceps roller and configured to detect a rotation angle of the forceps roller. The forceps encoder 82 is configured to output rotation angle data to a forceps detecting apparatus 83 of the control unit 24. Data of each length from the distal end portion to each forceps joint portion $88_1$ ... $88_5$ of the grasping forceps 36 and data of the total length of the forceps channel 35a are storage in the forceps detecting apparatus 83, the forceps detecting apparatus 83 is configured to calculate data of an amount of an insertion of the grasping forceps 36 on the basis of the input rotation angle data, and detect whether each of the forceps joint portions $88_1$ ... $88_5$ is projected from the distal end portion of the forceps channel 35a or not on the basis of the calculated data of an amount of an insertion, and each storage length data and the storage total length data. In this way, the forceps roller, the forceps encoder 82 and the forceps detecting apparatus 83 form a grasping portion projection and retraction detecting unit and a joint portion projection and retraction detecting unit configured to detect a projecting and a retracting of the grasping portion 38 and the forceps joint portion $88_1$ ... $88_5$ from the distal end portion of the forceps channel 35a. It is noted that a marker may be placed on the grasping forceps 36; a sensor configured to detect the marker may be provided on the forceps channel 35a, and an amount of an insertion of the grasping forceps 36 may be detected. Moreover, a marker may be placed on each forceps joint portion $88_1$ ... $88_5$, a sensor may be provided on the distal end portion of the forceps channel 35a, and it may be directly detected whether each of the forceps joint portions $88_1$ ... $88_5$ is projected from the distal end portion of the forceps channel 35a or not.

The forceps detecting apparatus 83 is configured to output detection data to the forceps control apparatus 49 and the display processor 30. Control by the forceps control apparatus 49 on the basis of the detection data will be explained below in detail. The display processor 30 is configured to display an animation and the like indicating a projecting state of the grasping forceps 36 from the distal end portion of the forceps channel 35a on the basis of the detection data.

On the other hand, an active high-frequency accessory 50 (simply referred to as a high-frequency accessory 50 hereinafter) as an accessory is adapted to be inserted through an accessory channel 35b of the endoscope 10 so as to be movable forward and backward. In the high-frequency accessory 50, a high-frequency electrode 52 to which a high-frequency current is adapted to be applied, an accessory bending portion 54 configured to be actuated to be bent and an accessory insertion tube portion 58 being long and flexible are provided in order from the distal end side.

Figure 4A:
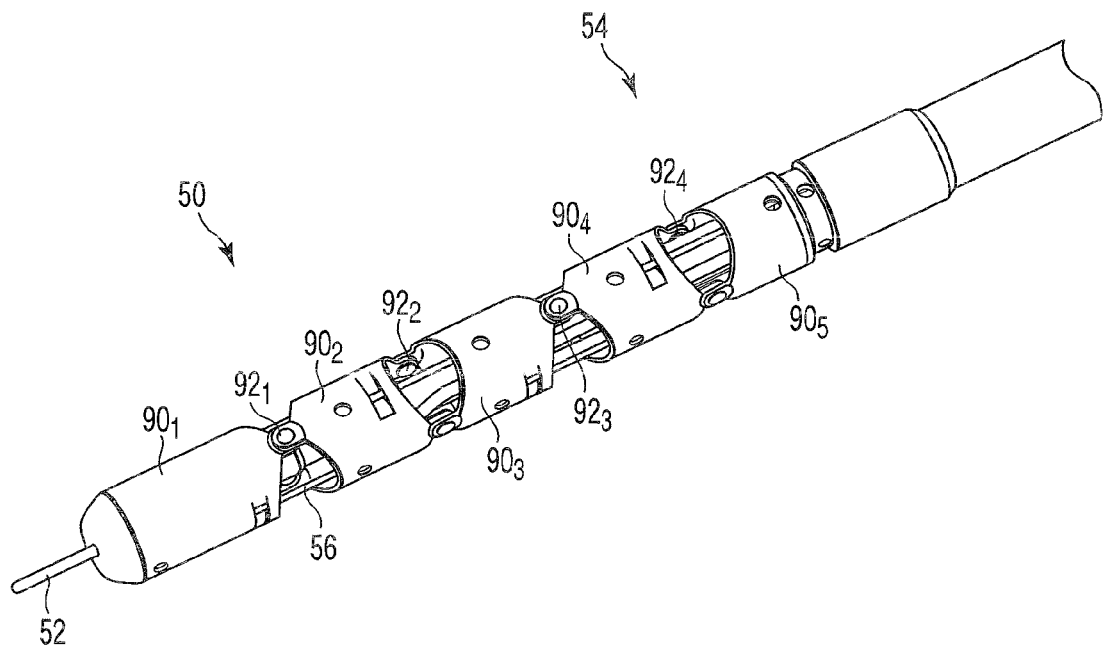
FIG. 4A is a perspective view showing a distal end portion of the high-frequency accessory according to the first embodiment of the present invention.
Figure 4B:
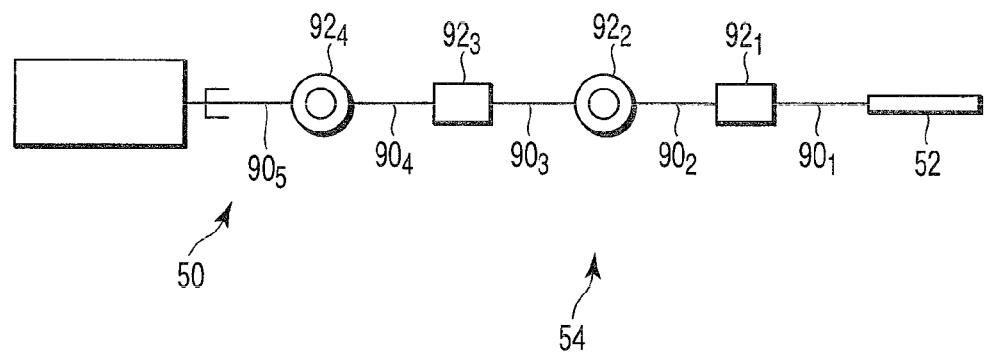
FIG. 4B is a schematic view showing the distal end portion of the high-frequency accessory according to the first embodiment of the present invention.

Referring to FIGS. 4A and 4B, a structure of the distal end portion of the high-frequency accessory 50 will be explained in detail.

In the distal end portion of the high-frequency accessory 50, the high-frequency electrode 52 is protruded from the distal end portion of a first accessory bending part $90_1$ so as to be movable forward and backward. The distal end portion of an accessory operation wire for operating the high-frequency electrode 52 to be moved forward and backward and applying a high-frequency current to the high-frequency electrode 52 is coupled to the proximal end portion of the high-frequency electrode 52.

Moreover, in the distal end portion of the high-frequency accessory 50, a first to a fifth substantially circular cylindrical accessory bending part $90_1$, $90_2$, $90_3$, $90_4$, $90_5$ is coupled in order through a first to a fourth accessory joint portion $92_1$, $92_2$, $92_3$, $92_4$. The first to fifth accessory bending part $90_1$ ... $90_5$ is rotatable relative to each other about a rotational axis of the first to the fourth accessory joint portion $92_1$ ... $92_4$, and the rotational axes of the accessory joint portions $92_1$ ... $92_4$ adjacent to each other are substantially orthogonal to each other. The distal end portions of accessory angle wires 56 for actuating the first to the fourth accessory joint portion $92_1$ ... $92_4$ to be rotated are connected to the first to the fourth accessory bending part $90_1$ ... $90_4$.

In this way, the high-frequency electrode 52 and the first to the fourth accessory joint portion $92_1$ ... $92_4$ form actuation portions, respectively. The accessory operation wire and the accessory angle wires 56 are inserted through the accessory bending portion 54 and the accessory insertion tube portion 58 and extended to the proximal end side.

Referring to FIGS. 1 and 2 again, the accessory insertion tube portion 58 is put out from the accessory insertion inlet 34b and extended to an accessory actuating apparatus 60 provided on the movable type of endoscope stand 22, and the accessory angle wires 56 are put out from the proximal end portion of the accessory insertion tube portion 58 and coupled to the accessory wire actuating apparatus 60. The accessory wire actuating apparatus 60 is connected to an accessory control apparatus 61 as a joint portion control unit of the control unit 24, and an accessory master arm 62 as a joint portion operating unit is connected to the accessory control apparatus 61. The accessory master arm 62 includes a degree of freedom similar to that of the accessory bending portion 54 of the active high-frequency accessory 50. When operating the accessory master arm 62, the accessory wire actuating apparatus 60 moves forward and backward the accessory angle wires 56 according to an operation to the accessory master arm 62 and the accessory bending portion 54 is actuated to be bent in the normal mode.

A resin tube 64 through which the accessory operation wires are inserted is extended from the proximal end portion of the accessory insertion tube portion 58. The accessory operation portion 68 is coupled to the proximal end portion of the resin tube 64, and the proximal end portion of the accessory operation wire is coupled to a slider 70 of the accessory operation portion 68. When moving forward and backward the slider 70 relative to the accessory operation portion main portion 72, the accessory operation wire is moved forward and backward. Moreover, a connecting terminal 74 is provided on the slider 70 and is electrically connected to the accessory operation wire. The connecting terminal 74 is connected to a high-frequency power source 78 through a power source code 76, and a high-frequency current is adapted to be applied to the high-frequency electrode 52 through the power source code 76 and the accessory operation wire from the high-frequency power source 78. It is noted that a foot switch 80 as a high-frequency electrode operating unit is connected to a power source control apparatus 79 as a high-frequency electrode control unit of the high-frequency power source 78, and the high-frequency power source 78 is configured to be actuated and stopped according to an operation to the foot switch 80 in the normal mode.

Furthermore, as is similar to the case of the grasping forceps 36, an accessory roller, an accessory encoder 84 and an accessory detecting apparatus 85 are configured to detect whether each of the distal end portion of the high-frequency accessory 50 and the accessory joint portions $92_1$ ... $92_4$ is projected from the distal end portion of the accessory channel 35b or not. That is, the accessory roller, the accessory encoder 84 and the accessory detecting apparatus 85 form a high-frequency electrode projection and retraction detecting unit and a joint portion projection and retraction detecting unit. As is similar to the case of the grasping forceps 36, a marker and a sensor may be used. Detection data is to be output to a power source control apparatus 79, the accessory control apparatus 61 and the display processor 30. Control by the power source control apparatus 79 and the accessory control apparatus 61 on the basis of the detection data will be explained below in detail. As is similar to the grasping forceps 36, the display apparatus 32 is configured to display an animation and the others indicating a projecting state of the high-frequency accessory 50 from the distal end portion of the accessory channel 35b on the basis of the detection data.

A personal computer 81 is connected to the control unit 24 and configured to perform various kinds of arithmetic and storage processing.

Next, a method for controlling the endoscope apparatus according to the embodiment will be explained.

Figure 5:
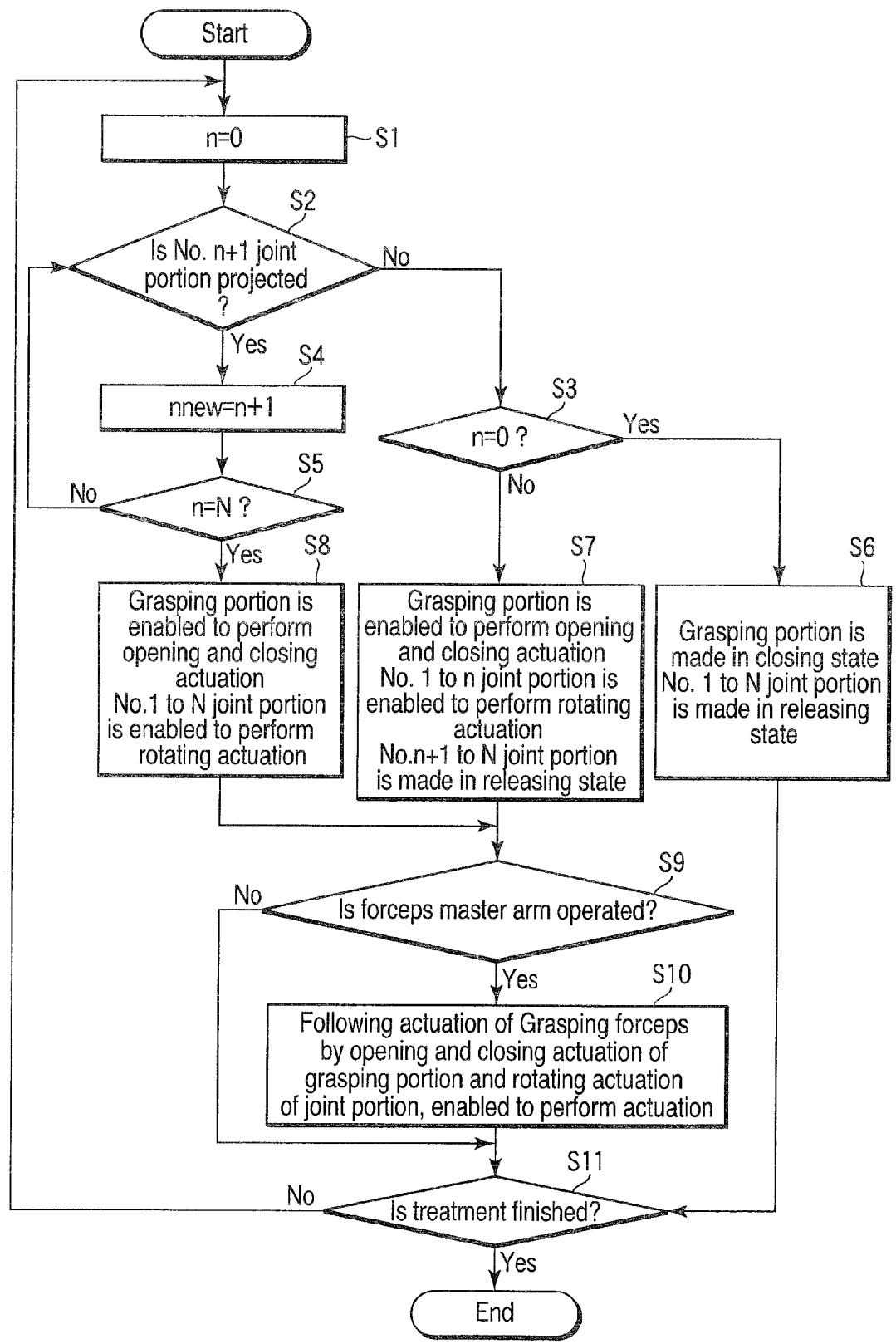
FIG. 5 is a flow chart for explaining control of the grasping forceps according to the first embodiment of the present invention.

Referring to a flow chart of FIG. 5, a method for controlling the grasping forceps 36 will be explained.

Steps 1 to 5 (S1 to S5)

It is detected what number forceps joint portion $88_1$ ... $88_N$ from the first forceps joint portion $88_1$ out of the No. 1 to N forceps joint portion $88_1$ ... $88_N$ (N=5) is projected from the distal end portion of the forceps channel 35a. The step advances to Step 6 (S6) when any forceps joint portion $88_1$ ... $88_N$ is not projected, the step advances to step 7 (S7) when the n forceps joint portion $88_n$ ($1 \leq n \leq N-1=4$) from the first forceps joint portion $88_1$ are projected, and the step advances to Step 8 (S8) when all forceps joint portions $88_1$ ... $88_N$ are projected.

Step 6 (S6)

Figure 6A:
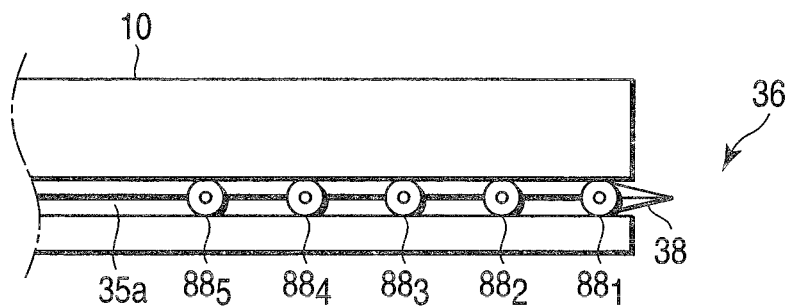
FIG. 6A is a schematic view showing a first projecting state of the grasping forceps according to the first embodiment of the present invention.

As is shown in FIG. 6A, when any forceps joint portion $88_1$ ... $88_N$ is not projected, the forceps control apparatus 49 is changed to a stopping mode. In the stopping mode, the grasping portion 38 is kept in a closing state, the No. 1 to N forceps joint portion $88_1$ ... $88_N$ is kept in a releasing state, regardless of an operation to the forceps master arm 48. When the No. 1 to N forceps joint portion $88_1$ ... $88_N$ is in the releasing state, the grasping portion 38 and the forceps bending portion 40 is passively deformed following a shape of the forceps channel 35a. Next, the step advances to Step 11 (S11).

Step 7 (S7)

Figure 6B:
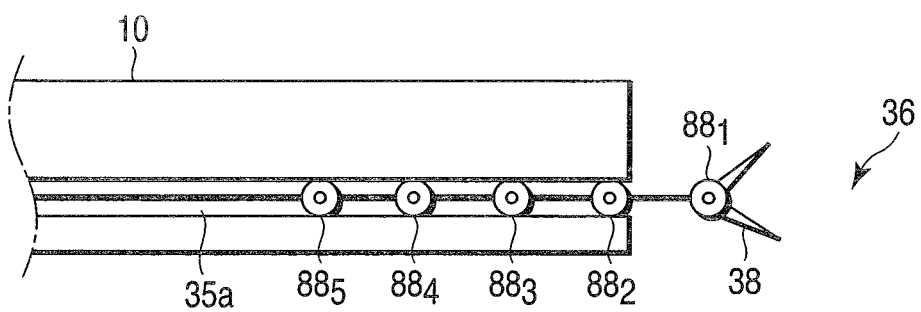
FIG. 6B is a schematic view showing a second projecting state of the grasping forceps according to the first embodiment of the present invention.
Figure 6C:
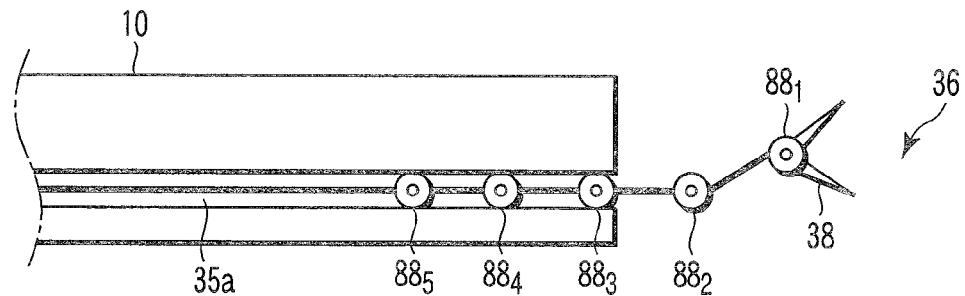
FIG. 6C is a schematic view showing a third projecting state of the grasping forceps according to the first embodiment of the present invention.

As is shown in FIGS. 6B and 6C, when the No. 1 to n forceps joint portion $88_1$ ... $88_n$ ($1 \leq n \leq N-1=4$) is projected, the forceps control apparatus 49 is changed to No. n actuating mode ($1 \leq n \leq N-1=4$). In the No. n actuating mode; the grasping portion 38 can be actuated to be opened and closed according to an operation to the forceps master arm 48, and the No. 1 to n forceps joint portion $88_1$ ... $88_n$ can be actuated to be rotated according to an operation to the forceps master arm 48. On the other hand, the No. n+1 to N forceps joint portion $88_{n+1} \ldots 88_N$ is kept in the releasing state regardless of an operation to the forceps master arm 48. When the No. n+1 to N forceps joint portion $88_{n+1} \ldots 88_N$ is in the releasing state, the forceps bending portion 40 in the forceps channel 35a is passively deformed following a shape of the forceps channel 35a. Next, the step advances to Step 9 (S9).

Step 8 (S8)

Figure 6D:
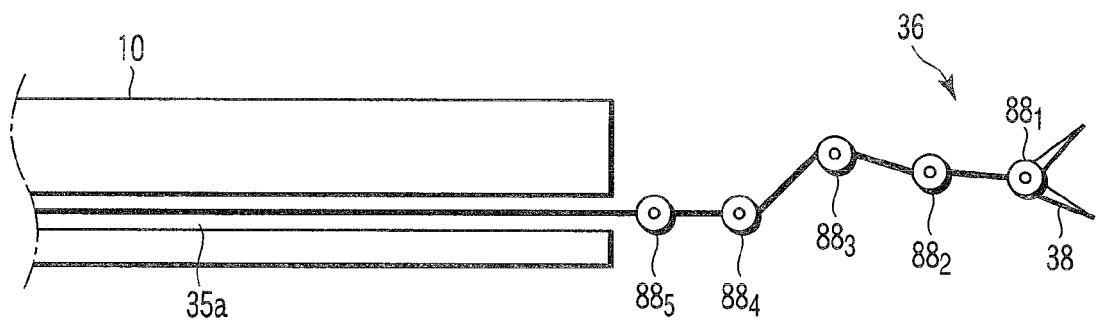
FIG. 6D is a schematic view showing a fourth projecting state of the grasping forceps according to the first embodiment of the present invention.

As is shown in FIG. 6D, when all forceps joint portions $88_1 \ldots 88_N$ are projected, the forceps control apparatus 49 is changed to No. N actuating mode (N=5), that is, the normal mode. In the No. N actuating mode, the grasping portion 38 can be actuated to be opened and closed according to an operation to the forceps master arm 48, and all forceps joint portions $88_1 \ldots 88_N$ can be actuated to be rotated according to an operation to the forceps master arm 48. Next, the step advances to Step 9 (S9).

Steps 9 and 10 (S9 and S10)

The grasping portion 38 and the forceps joint portion $88_1 \ldots 88_N$ which can be actuated are actuated to be opened and closed, and rotated, and the grasping forceps 36 is made to perform a following actuation according to an operation to the forceps master arm 48.

Step 11 (S11)

The above steps are repeated until treatment is Hereinafter, control equations of the No. 1 to N forceps joint portion $88_1 \ldots 88_N$ in the No. n actuating mode (1≤n≤N=5) will be explained. A positional attitude E of the grasping portion 38 is expressed by joint parameter Φ as follows:

E=A(Φ);

E (x, v. Z, $\theta_{Roll}$, $\theta_{Yaw}$, $\theta_{pitch}$)T;

Φ=($\phi_1$, $\phi_2$, ..., $\phi_{N-1}$, $\phi_N$);

x, y, and z: coordinates of the grasping portion 38 relative to the proximal end portion of the forceps bending portion 40;

$\theta_{Roll}$, $\theta_{Yaw}$, and $\theta_{Pitch}$: a roll angle, a yaw angle, and a pitch angle of the grasping portion 38;

$\phi_s$: a rotation angle of the No. s forceps joint portion $88_s$. Here, in the No. n actuating mode, regarding the joint parameter Φ, $\phi_1 \ldots \phi_n$ are variables and $\phi_{n+1} \ldots \phi_N$ are certain invariables determined on the basis of a shape of the forceps channel 35a. With regard to a target positional attitude $E_P$ input by the forceps master arm 48, it is necessary to find joint parameter $\Phi_P$ satisfying with the following equation, $E_P = A(\Phi_P)$.

It is possible to calculate $\Phi_P$ by performing a convergent calculation using a present positional attitude $E_{now}$, a target positional attitude $E_P$ and a present joint parameter $\Phi_{now}$ as boundary the basis of the following equation:

$d\Phi = J(\Phi)^{-1} dE$;

J(Φ): Jacobian matrix obtained by partially differentiating E (=A(Φ)) with respect to variable components of Φ.

As is mentioned above, the control equations of the grasping forceps 36 are switched according to the actuating modes.

Hereinafter, a drawing actuation of the grasping forceps 36 will be explained.

Even when the whole distal end portion of the grasping forceps 36 is projected from the distal end portion of the forceps channel 35a and the grasping portion 38 or the first to fifth forceps joint portion $88_1 \ldots 88_5$ is in the open state or the rotating state, the grasping forceps 36 can be drawn into the forceps channel 35a. That is, as the forceps insertion tube portion 44 is operated to be moved backward and the grasping forceps 36 is drawn into the forceps channel 35a, the fourth forceps joint portion $88_4$ is drawn into the forceps channel 35a next the fifth forceps joint portion $88_5$ and made in the releasing state, and the third forceps bending part $86_3$ is drawn into the forceps channel 35a while urged by the inner surface of the forceps channel 35a and rotated following a shape of the forceps channel 35a relative to the fourth forceps bending part $86_4$. Next, the third and the second forceps joint portion $88_3$ and $88_2$ is made in the releasing state in order, the third and the second forceps bending part $86_3$ and $86_2$ are drawn into the forceps channel 35a in order while rotated following a shape of the forceps channel 35a. When the first forceps joint portion $88_1$ is drawn into the forceps channel 35a, the grasping portion 38 is actuated to be closed and the whole grasping portion 38 is rotated relative to the first forceps bending part $86_1$ following a shape of the forceps channel 35a, and the grasping portion 38 is drawn into the forceps channel 35a. In this way, when drawing the grasping forceps 36, a shape of the distal end portion of the grasping forceps 36 is passively deformed following a shape of the forceps channel 35a.

Figure 7:
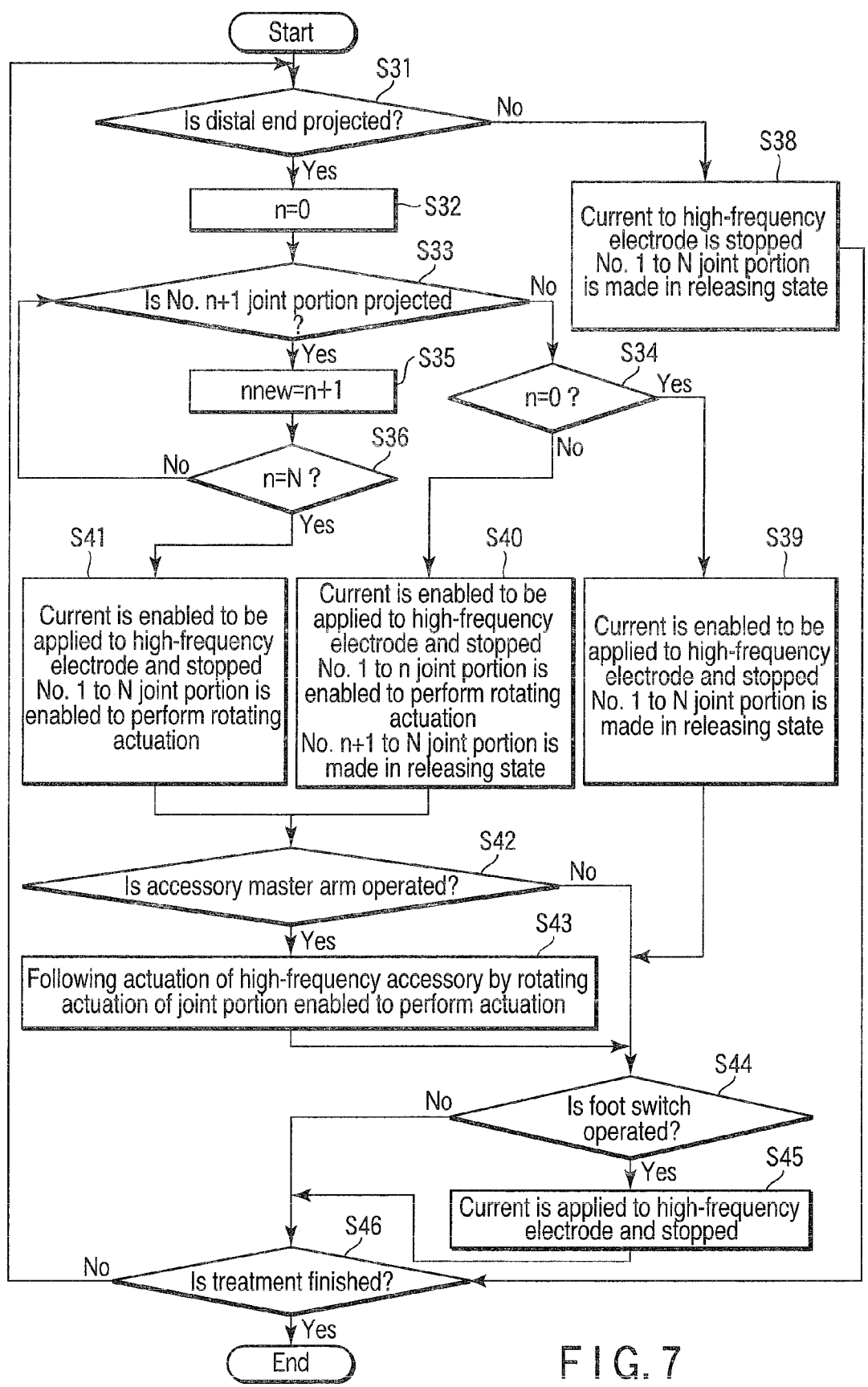
FIG. 7 is a flow chart explaining control of the high-frequency accessory according to the first embodiment of the present invention.

Next, referring to a flow chart of FIG. 7, a method for controlling the high-frequency accessory 50 will be explained.

Step 31 (S31)

It is detected whether the distal end portion of the first accessory bending part $90_1$ is projected from the accessory channel 35b. The step advances to Step 38 (S38) when it is not projected and the step advances to Step 32 (S32) when it is projected.

Steps 32 to 36 (S32 to S36)

It is detected what number accessory joint portion $92_1 \ldots 92_N$ from the first accessory joint portion $92_1 \ldots 92_N$ out of the No. 1 to N accessory joint portion $92_1 \ldots 92_N$ (N=4) is projected from the distal end portion of the accessory channel 35b. The step advances to Step 39 (S39) when any accessory joint portion $92_1 \ldots 92_N$ is not projected, the step advances to Step 40 (S40) when the No. 1 to n accessory joint portion $92_n$ (1≤n≤N−1=3) are projected; and the step advances to Step 41 (S41) when all accessory joint portion $92_1 \ldots 92_N$ are projected.

Step 38 (S38)

When the distal end portion of the first accessory bending part $90_1$ is projected from the accessory channel 35b, the power source control apparatus 79 and the accessory control apparatus 61 are changed to a stopping mode. In the stopping mode, a high-frequency current to the high-frequency electrode 52 is stopped regardless of an operation to the foot switch 80, and also, all accessory joint portions $92_1 \ldots 92_N$ are kept in the releasing state regardless of an operation to the accessory master arm 62. As is similar to the case of the grasping forceps 36, when all accessory joint portions $92_1 \ldots 92_N$ are kept in the releasing state, the accessory bending portion 54 is passively deformed following a shape of the accessory channel 35b. Next, the step advances to step 46 (S46).

Step 39 (S39)

When the distal end portion of the first accessory bending part $90_5$ is projected from the accessory channel 35b and any accessory joint portion $92_1 \ldots 92_N$ is not projected, the power source control apparatus 79 and the accessory control apparatus 61 are changed to No. 0 actuating mode. In the No. 0 actuating mode, a high-frequency current can be applied to the high-frequency electrode 52 and stopped according to an operation to the foot switch 80. The same is true of No. 1 to N actuating mode below. Moreover, in the No. 0 actuating mode, as is similar to the stopping mode, all accessory joint portions $92_1 \ldots 92_N$ is kept in the releasing state regardless of an operation to the accessory master arm 62. Next, the step advances to step 44 (S44).

Step 40 (S40)

When the No. 1 to n accessory joint portion $92_1 \ldots 92_n$ ($1 \le n \le N-1=3$) is projected, the power source control apparatus 79 and the accessory control apparatus 61 are changed to No. n actuating mode ($1 \le n \le N-1=3$). In the No. n actuating mode, the No. 1 to n accessory joint portion $92_1 \ldots 92_n$ can be actuated to be rotated according to an operation to the accessory master arm 62. On the other hand, the No. n+1 to N accessory joint portion $92_{n+1} \ldots 92_N$ is kept in the releasing state regardless of an operation to the accessory master arm 62, a shape of the accessory bending portion 54 is passively deformed following a channel 35b. Next, the step advances to Step 42 (S42).

Step 41 (S41)

When all accessory joint portions $92_1 \ldots 92_N$ are projected, the power source control apparatus 79 and the accessory control apparatus 61 are changed to No. N actuating mode (N=4), that is, the normal mode. In the No. N actuating mode, all accessory joint portion $92_1 \ldots 92_N$ can be actuated to be rotated according to an operation to the accessory master arm 62. Next, the step advances to Step 42 (S42).

Steps 42 and 43 (S42 and S43)

The accessory joint portions $92_1 \ldots 92_N$ which can be actuated are actuated to be rotated according to an operation to the accessory master arm 62, and the high-frequency accessory 50 is made to perform a following actuation.

Steps 44 and 45 (S44 and S45)

A high-frequency current is applied to the high-frequency electrode 52 and stopped according to an operation to the foot switch 80.

Step 46 (S46)

The above steps are repeated until treatment is finished.

Control equations of the No. 1 to N accessory joint portion $92_1 \ldots 92_N$ in the No. n actuating mode ($1 \le n \le N=4$) are similar to the control equations of the grasping forceps 36. Moreover, a drawing actuation of the high-frequency accessory 50 is similar to the drawing actuation of the grasping forceps 36. As the high-frequency accessory 50 is drawn into the accessory channel 35b in the state where a high-frequency current is applied to the high-frequency electrode 52, a high-frequency current to the high-frequency electrode 52 is stopped in the point of time when the distal end portion of the first accessory bending part $90_1$ is drawn into the accessory channel 35b.

Therefore, the endoscope apparatus according to the embodiment exhibit following effects.

In the endoscope apparatus according to the embodiment, it is detected whether the grasping portion 38 of the grasping forceps 36 is projected from the forceps channel 35a or not, and then, the grasping portion 38 is enabled to be actuated to be opened and closed according to an operation to the forceps master arm 48 when it is projected, and the grasping portion 38 is made in the closing state regardless of an operation to the forceps master arm 48 when it is not projected. Moreover, it is detected whether the high-frequency electrode 52 of the high-frequency accessory 50 is projected from the accessory channel 35b or not, and then, a high-frequency current is enabled to be applied to the high-frequency electrode 52 and stopped according to an operation to the foot switch 80 when it is projected, and a high-frequency current to the high-frequency electrode 52 is stopped regardless of an operation to the foot switch 80 when it is not projected. Furthermore, it is detected whether the forceps joint portion $88_1 \ldots 88_5$ or the accessory joint portion $92_1 \ldots 92_4$ is projected from the forceps channel 35a or the accessory channel 35b or not, and then, the forceps joint portion $88_1 \ldots 88_5$ or the accessory joint portion $92_1 \ldots 92_N$ is enabled to be actuated to be rotated according to an operation to the forceps master arm 48 or the accessory master arm 62 when it is projected, and the forceps joint portion $88_1 \ldots 88_5$ or the accessory joint portion $92_1 \ldots 92_N$ is made in the releasing state regardless of an operation to the forceps master arm 48 or the accessory master arm 62 when it is not projected. Therefore, an operability of the endoscope apparatus is improved in comparison with the case where an operator by oneself judges whether each of the grasping portion 38, the forceps joint portions $88_1 \ldots 88_5$, the high-frequency electrode 52 and the accessory joint portions $92_1 \ldots 92_N$ is projected or not and operate on the basis of a result of the judgment. Moreover, an opening actuation of the grasping portion 38, a rotating actuation of the forceps joint portions $88_1 \ldots 88_5$, an application of a high-frequency current to the high-frequency accessory 50 and a rotating actuation of the accessory joint portions $92_1 \ldots 92_N$ in the forceps channel 35a or the accessory channel 35b are avoided, and therefore, it is prevented that the forceps channel 35a, the grasping portion 38, the forceps joint portions $88_1 \ldots 88_5$, the accessory channel 35b, the high-frequency electrode 52 and the accessory joint portions $92_1 \ldots 92_N$ are damaged.

Moreover, only the forceps joint portion $88_1 \ldots 88_5$ projected from the distal end portion of the forceps channel 35a out of the plurality of forceps joint portions $88_1 \ldots 88_5$ of the grasping forceps 36 is actuated to be rotated. Therefore, an operability of the endoscope apparatus is sufficiently improved in comparison with the case where an operator by oneself selects which forceps joint portions $88_1 \ldots 88_5$ is to be actuated to be rotated out of the plurality of forceps joint portions $88_1 \ldots 88_5$ and actuates it to be rotated in order that the forceps channel 35a and the grasping forceps 36 is not damaged. The same is true of the high-frequency accessory 50.

Furthermore, when the forceps joint portion $88_1 \ldots 88_5$ of the grasping forceps 36 is made in the releasing state, a shape of the grasping forceps 36 is passively deformed following a shape of the forceps channel 35a, and therefore, the control of the forceps joint portion $88_1 \ldots 88_5$ is sufficiently simple. The same is true of the high-frequency accessory 50.

Hereinafter, a second embodiment of the present invention will be explained.

In the embodiment, forceps joint portions $88_1 \ldots 88_5$ is actively actuated to be rotated such that a shape of the distal end portion of a grasping forceps 36 is actively deformed following a shape of a forceps channel 35a. That is, the distal end portion of the forceps channel 35a is substantially straight, and a grasping portion 38 and a forceps bending portion 40 of the grasping forceps 36 can be placed in the straight part. When the No. n forceps joint portion $88_n$ ($1 \le n \le 5$) is place in the straight part of the forceps channel 35a, a rotation angle of the No. n forceps joint portion $88_n$ is made to be substantially 0, and the grasping portion 38 or forceps bending part $86_1 \ldots 86_5$ on the distal end side and the proximal end side of the No. n forceps joint portion $88_n$ are placed so as to be straight relative to each other. In a drawing actuation of the grasping forceps 36, when the No. n forceps joint portion $88_n$ is drawn into the forceps channel 35a, a rotation angle of the No. n forceps joint portion $88_n$ is made to be substantially 0, and the grasping portion 38 or the forceps bending part $86_1 \ldots 86_5$ on the distal end side of the No. n forceps joint portion $88_n$ is placed so as to be straight relative to the forceps bending part $86_1 \ldots 86_5$ on the proximal end side. In this way, when drawing the grasping forceps 36, the grasping forceps 36 and the forceps channel 35a are not interfered to each other, and a shape of the distal end portion of the grasping forceps 36 is actively deformed following a shape of the forceps channel 35a.

The high-frequency accessory 50 is actuated similarly to the grasping forceps 36.

Therefore, the endoscope apparatus according to the embodiment exhibits the following effect.

In the endoscope apparatus according to the embodiment, the forceps joint portions $88_1 \ldots 88_5$ are actuated to be rotated such that a shape of the distal end portion of the grasping forceps 36 is actively deformed following a shape of the forceps channel 35a, and therefore, the grasping forceps 36 and the forceps channel 35a are hardly interfered to each other, and it is sufficiently prevented that the grasping forceps 36 and the forceps channel 35a is damaged. The same is true of the high-frequency accessory 50.

Hereinafter, a modified example of the second embodiment of the present invention will be explained.

A tension sensor is provided on an endoscope wire actuating apparatus 23 and configured to detect tension of endoscope angle wires and the tension sensor is configured to output tension data to an endoscope control apparatus 25. The endoscope control apparatus 25 is configured to calculate bending shape data indicating a bending shape of an endoscope bending portion 16 on the basis of the input tension data. A distal end shape data indicating a shape of the forceps channel 35a in a distal end rigid portion 14 is previously storage in a forceps control apparatus 49 and the bending shape data is input to the forceps control apparatus 49. The forceps control apparatus 49 is configured to calculate shape data indicating a shape of the forceps channel 35a on the basis of distal end shape data and bending shape data. Moreover, data of an amount of an insertion of the grasping forceps 36 is to be input to the forceps control apparatus 49 from a forceps detecting apparatus 83. The forceps control apparatus 49 is configured to make forceps joint portions $88_1 \ldots 88_5$ perform active rotating actuations such that a shape of the distal end portion of the grasping forceps 36 is actively deformed following a shape of the forceps channel 35a on the basis of the shape data of the forceps channel 35a and the data of the amount of the insertion of the grasping forceps 36.

The high-frequency accessory 50 is actuated similarly to the grasping forceps 36.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope apparatus comprising:
   an accessory including an actuation portion configured to be actuated;
   an operating unit configured to operate the actuation portion;
   an endoscope including an accessory insertion pass wherein the accessory is adapted to be inserted through the accessory insertion pass from a proximal end portion of the accessory insertion pass to a distal end portion of the accessory insertion pass, and projected from and retracted into the distal end portion of the accessory insertion pass;
   a detecting unit configured to detect a condition of a part of the accessory, which is projected from the distal end portion of the accessory insertion pass; and
   a control unit configured to control an actuation of the actuation portion by an operation to the operating unit, on the basis of a result of detection by the detecting unit;
   wherein the accessory includes an active accessory,
   the actuation portion includes a plurality of joint portions configured to be actuated to make the active accessory perform an active movement,
   the operating unit is configured to individually operate the plurality of joint portions,
   the detecting unit is configured to detect individual joint portions of the plurality of joint portions which are projected from the distal end portion of the accessory insertion pass, and individual joint portions of the plurality of joint portions which are not projected from the distal end portion of the accessory insertion pass, and
   wherein the control unit is configured to actuate only the individual joint portions of the plurality of joint portions according to an operation to the operating unit for the individual joint portions which are detected to be projected from the distal end portion of the accessory insertion pass, and configured to maintain the individual joint portions not projected from the distal end portion of the accessory insertion pass in a non-actuated state, wherein in the non-actuated state, the individual joint portions are prevented from being actuated by the operation unit regardless of an operation by the operation unit and the individual joint portions are deformed to match a shape of the accessory insertion pass.

2. The endoscope apparatus according to claim 1,
   wherein the active accessory includes a grasping forceps,
   the plurality of joint portions include a grasping portion disposed at a distal most end of the plurality of joint portions, the grasping portion being configured to be actuated to be opened and closed,
   the operating unit is configured to operate the grasping portion to be opened and closed,
   the detecting unit is configured to detect whether the grasping portion is projected from the distal end portion of the accessory insertion pass, and
   the control unit is configured to make the grasping portion perform an opening and closing actuation according to an operation to the operating unit when the detecting unit detects that the grasping portion is projected from the distal end portion of the accessory insertion pass, and configured to maintain the grasping portion in a closing state regardless of an operation to the operating unit when the detecting unit detects that the grasping portion is not projected from the distal end portion of the accessory insertion pass.

3. The endoscope apparatus according to claim 1,
   wherein the accessory includes a high-frequency accessory,
   the actuation portion includes a high-frequency electrode wherein a high-frequency current is adapted to be applied to the high-frequency electrode and stopped,
   the operating unit includes a high-frequency electrode operating unit configured to operate an applying and a stopping of a high-frequency current to the high-frequency electrode,
   the detecting unit includes a high-frequency electrode projection and retraction detecting unit configured to detect whether the high-frequency electrode is projected from the distal end portion of the accessory insertion pass or not, and
   the control unit includes a high-frequency electrode control unit configured to apply and stop a high-frequency current to the high-frequency electrode according to an operation to the high-frequency electrode operating unit when the high-frequency electrode projection and retraction detecting unit detects that the high-frequency electrode is projected, and stop a high-frequency current to the high-frequency electrode regardless of an operation to the high-frequency electrode operating unit when the high-frequency electrode projection and retraction detecting unit detects that the high-frequency electrode is not projected.

4. The endoscope apparatus according to claim 1, wherein the non-actuated state of the individual joint portions include an active actuating state where the individual joint portions detected not to be projected from the distal end portion of the accessory insertion pass are actuated such that a shape of the active accessory is actively deformed following a shape of the accessory insertion pass.

5. The endoscope apparatus according to claim 1, wherein the non-actuated state of the individual joint portions include a released state where the individual joint portions detected not to be projected from the distal end portion of the accessory insertion pass are released to passively deform to the shape of the accessory insertion pass.

6. The endoscope apparatus according to claim 1, wherein the control unit is configured to actuate all of the individual joint portions of the plurality of joint portions according to an operation to the operating unit where all of the individual joint portions are detected to be projected from the distal end portion of the accessory insertion pass.

7. The endoscope apparatus according to claim 1, wherein when the detecting unit detects that none of the individual joint portions are projected from the distal end portion of the accessory insertion pass, the control unit is configured to maintain all of the individual joint portions in a non-actuated state, wherein in the non-actuated state, all of the individual joint portions are prevented from being actuated by the operation unit regardless of an operation by the operation unit and all of the individual joint portions are deformed to match a shape of the accessory insertion pass.

8. The endoscope apparatus according to claim 7, wherein the non-actuated state of the individual joint portions include an active actuating state where the individual joint portions detected not to be projected from the distal end portion of the accessory insertion pass are actuated such that a shape of the active accessory is actively deformed according to a shape of the accessory insertion pass.

9. The endoscope apparatus according to claim 7, wherein the non-actuated state of the individual joint portions include a released state where the individual joint portions detected not to be projected from the distal end portion of the accessory insertion pass are released to passively deform to the shape of the accessory insertion pass.

* * * * *